United States Patent
McCombs et al.

(10) Patent No.: US 8,267,975 B2
(45) Date of Patent: Sep. 18, 2012

(54) BONE SCREW SYSTEM

(75) Inventors: Mary McCombs, Lakeland, TN (US);
Aaron C. Smith, Arlington, TN (US);
James A. Nunley, Durham, NC (US)

(73) Assignee: Wright Medical Technology, Inc.,
Arlington, TN (US)

( * ) Notice: Subject to any disclaimer, the term of this patent is extended or adjusted under 35 U.S.C. 154(b) by 0 days.

(21) Appl. No.: 13/219,765

(22) Filed: Aug. 29, 2011

(65) Prior Publication Data
US 2011/0313469 A1 Dec. 22, 2011

Related U.S. Application Data

(63) Continuation of application No. 12/051,977, filed on Mar. 20, 2008.

(60) Provisional application No. 60/895,799, filed on Mar. 20, 2007.

(51) Int. Cl.
*A61B 17/04* (2006.01)

(52) U.S. Cl. ......... 606/300; 411/378; 411/393; 606/301

(58) Field of Classification Search ............... 606/62, 606/64, 76, 69, 102, 300, 301, 53, 60, 79, 606/86, 72, 73, 65; 433/173–176; 411/414, 411/423–424
See application file for complete search history.

(56) References Cited

U.S. PATENT DOCUMENTS

| | | | |
|---|---|---|---|
| 5,334,204 A | | 8/1994 | Clewett et al. |
| 5,336,225 A | * | 8/1994 | Zang ........................ 606/304 |
| 5,643,269 A | | 7/1997 | Harle |
| 6,325,583 B1 | | 12/2001 | Mattle et al. |
| 6,503,252 B2 | | 1/2003 | Hansson |
| 2004/0006345 A1 | | 1/2004 | Vlahos et al. |
| 2004/0172022 A1 | | 9/2004 | Landry et al. |

OTHER PUBLICATIONS

Nunley, J.A., M.D., "Fractures of the Base of the Fifth Metatarsal", Foot and Ankle Trauma, Jan. 2001, 31 (1):171-180, American Orthopedic Foot and Ankle Society, Inc., Durham, N.C.
Kelly, et al., "Intramedullary Screw Fixation of Jones Fractures", Foot & Ankle International, Jul. 2001, 22:(7):585-589, American Orthopedic Foot and Ankle Society, Inc., Durham, N.C.

* cited by examiner

*Primary Examiner* — Thomas Barrett
*Assistant Examiner* — Melissa A Golob
(74) *Attorney, Agent, or Firm* — Duane Morris LLP

(57) ABSTRACT

A set of screws sized and configured for fixing a Jones fracture in a fifth metatarsal bone of a patient by preserving a bone thread path. Each screw has a low profile head on a trailing end, a thread portion on a leading portion, and a smooth shank portion between the head portion and the thread portion. A first screw has a thread major diameter of between about 4.4-4.6 mm, a second screw a thread major diameter of between about 5.4-5.6 mm, and a third screw a thread major diameter of between about 6.4-6.6 mm. The thread portion of all the screws in the set has a set of identical thread profile characteristics comprising a pitch, a leading edge angle, a trailing edge angle, a leading edge radius, a trailing edge radius, and a land. Each screw size is provided in various preferred lengths.

20 Claims, 6 Drawing Sheets

BONE SCREW SYSTEM

CROSS REFERENCE TO RELATED APPLICATIONS

This application is a continuation of U.S. patent application Ser. No. 12/051,977, which was filed on Mar. 20, 2008 claiming priority to Provisional Patent Application Ser. No. 60/895,799, filed Mar. 20, 2007, the entireties of which are herein incorporated by reference.

STATEMENT REGARDING FEDERALLY SPONSORED RESEARCH

Not applicable

REFERENCE TO A MICROFICHE APPENDIX

Not applicable

FIELD OF THE INVENTION

The present invention relates to surgical kits, instruments, implants and methods, and more particularly to surgical kits, instruments, implants and methods for treating Jones fractures.

BACKGROUND OF THE INVENTION

A Jones Fracture is clinically described as a fracture approximately 12 mm from the base of the 5th metatarsal. The fracture typically extends laterally across the 5th metatarsal originating at the cuboid/4th metatarsal joint. Background about the history, anatomy and repair of Jones fractures is provided in *Fractures of the Base of the Fifth Metatarsal*, Foot and Ankle Trauma, 32:171-180, 2001 (Nunley, James A, M.D.), which is incorporated herein by reference.

Jones fractures are often a sports related injury. They commonly occur when an athlete twists the ankle, rolling it laterally over the talus. The resulting forces break the 5th metatarsal.

Jones fractures have a high non-union rate, reported in some studies as up to 50%. There are several reasons for the high non-union rate. A Jones fracture is located in an area of poor blood supply. In addition, several tendons attach in the area, and the tendons tend to pull the fracture apart, causing motion at the site of healing. Complications of surgery are not uncommon, and include damage to the sural nerve and peroneous brevis tendon.

Jones fractures in non-athletes are often treated with a cast or walking boot. The cast or walking boot will typically be maintained for 6-8 weeks, but patients sometimes spend up to 20 weeks in a cast. Often the fracture becomes a chronic non-union and surgery is recommended. Surgery is often performed on athletes in hopes of a quicker recovery and because the nonunion rate is so high. Surgical treatment commonly consists of fixing the fracture with a screw in the center of the intramedullary canal. The surgical technique is challenging mainly because of the shape of the 5th metatarsal bone. The 5th metatarsal has a lateral bow on the dorsoplanter plane and a dorsal bow on the medolateral plane. Additionally, the bone is irregular and pyramid shaped in the vertical cross section. Screw sizing is very important. If the screw is too long, it pierces the medial cortex and can even stress fracture later. If the screw diameter is too small, it will not grab the cortical bone, resulting in poor compression and fixation.

Treatment of Jones Fractures has been a difficult challenge for foot and ankle specialists. Existing systems suffer from various drawbacks, including: screw systems that are not designed specifically for Jones fractures; screws lacking optimal dimensions for Jones fractures; lack of appropriate screw size range; lack of custom instruments; use of cannulated screws, which are not as strong in fatigue as an equivalent solid screw; and use of fully threaded screws, which do not tolerate bending stress as well as a partially threaded screw. The optimal screw type for Jones screws has yet to be defined. See *Intramedullary Screw Fixation of Jones Fractures*, 22 Foot & Ankle Intl, No. 7, pp. 585-589 (2001). There is thus a need for the surgical kits, instruments, implants and methods having the following characteristics and improvements over the prior art.

OBJECTS AND SUMMARY OF THE INVENTION

It is an object of the invention to provide a set of screws specialized for use in fixing Jones fractures via placement in the intramedullary canal of the fifth metatarsal.

It is another object of the invention to provide methods for preparing the fifth metatarsal for implantation of the screws, sizing for a final screw implant, and implanting a final screw implant.

The foregoing and other objects and objectives are achieved by providing a set of screws sized and configured for fixing a Jones fracture in a fifth metatarsal bone of a patient. Each screw in the set has a low profile head on a trailing end, a thread portion on a leading portion, and a smooth shank portion between the head portion and the thread portion. A first screw of the set of screws has a thread major diameter of between about 4.4 mm to about 4.6 mm. A second screw of the set of screws has a thread major diameter of between about 5.4 mm to about 5.6 mm. A third screw of the set has a thread major diameter of between about 6.4 mm to about 6.6 mm.

The thread portion of all the screws in the set has a set of identical thread profile characteristics, the set of identical thread profile characteristics comprising a pitch, a leading edge angle, a trailing edge angle, a leading edge radius, a trailing edge radius, and a land. In one preferred embodiment, the first screw has a thread major diameter of about 4.5 mm, the second screw has a thread major diameter of about 5.5 mm, and the third screw has a thread major diameter of about 6.5 mm. The first screw preferably has a shank diameter of 3.2 mm and a thread minor diameter of 3.2 mm, the second screw preferably has a shank diameter of 3.5 mm and a thread minor diameter of 3.5 mm, and the third screw preferably has a shank diameter of 3.8 mm and a thread minor diameter of 3.8 mm. In a preferred embodiment, the identical thread profile characteristics comprise the pitch being between about 2 to about 2.5 mm; the leading edge angle being between about 60 to about 70 degrees, the trailing edge angle being between about 90 to about 100 degrees, the leading edge radius being about 0.8 mm, the trailing edge radius being about 0.3 mm; and the land being about 0.18 mm. In a most preferred embodiment, the pitch is about 2.2 mm, the leading edge angle is about 65 degrees, and the trailing edge angle is about 95 degrees. The leading edge of the thread may have a surface that is substantially flat except in a region of the leading edge radius, and the trailing edge of the thread may have a surface that is substantially flat except in a region of the trailing edge radius. The thread is preferably a sharp cancellous thread form, such as an HB type bone screw thread under ASTM F543-02 and ISO 5835 standards.

In order to accommodate patients of various sizes and fractures located at various places along the fifth metatarsal, each of the first, second and third screws is provided in a plurality of screw lengths for use in fixing fractures in a variety of fifth metatarsal bones. The screw lengths are preferably 40 mm, 45 mm, 50 mm, 55 mm, 60 mm, 65 mm and 70 mm. The thread portion preferably has a thread portion length of between about 12.7 mm to about 25.4 mm. More particularly, in a preferred set, the thread portion length is about 14 mm for each screw having a screw length of 40 mm, the thread portion length is about 15.7 mm for the screw having a screw length of 45 mm, the thread portion length is about 15.5 mm for the screw having a screw length of 50 mm, the thread portion length is about 19.3 mm for the screw having a screw length of 55 mm, the thread portion length is about 21.1 mm for the screw having a screw length of 60 mm, the thread portion length is about 22.9 mm for the screw having a screw length of 65 mm, and the thread portion length is about 24.6 mm for the screw having a screw length of 70 mm.

The low-profile head of the screw preferably has a generally hemi-spherical configuration, with a generally flat trailing end and a generally spherical leading edge. A radius of the spherical leading edge may substantially match a radius of the low profile head and originate along a lengthwise axis of the screw between about 0 mm to about 0.76 mm from the trailing end of the head. The low-profile head may have an outer diameter of between about 7.0 mm to about 9.0 mm. In a preferred embodiment, the low-profile head of the first screw has an outer diameter of about 7.2 mm and a leading edge radius of about 3.4 mm, the low-profile head of the second screw has an outer diameter of about 7.4 mm and a leading edge radius of about 3.7 mm, and the low-profile head of the third screw has an outer diameter of about 8.1 mm and a leading edge radius of about 4.1 mm.

A trailing end of the thread preferably has reverse cutting flutes configured for use in cutting bone during removal of the screw, to thereby assist with removal of the screws from the patient after bone in-growth has occurred. The screws may consist of solid surgical grade stainless steel. The screws may consist of solid titanium.

Methods of preparing the fifth metatarsal for implantation, sizing, and implanting a final screw are also provided. In general, a surgeon inserts the first tap into and through an intramedullary canal of the proximal bone fragment of the fifth metatarsal, then threads the distal tap thread portion of the first tap into an intramedullary canal of the distal bone fragment, to thereby form a bone thread path in the intramedullary canal of the fifth metatarsal bone. The surgeon determines whether the first tap is undersized for the fifth metatarsal bone of the patient. If so, the surgeon removes the first tap from the fifth metatarsal bone and inserts the second tap into and through the intramedullary canal of the proximal bone fragment. The surgeon threads the distal tap thread portion of the second tap into the bone thread path in the intramedullary canal of the distal bone fragment. Due to the configuration of the screws of the set, the distal tap thread portion of the second tap preserves the bone thread path while also axially enlarging an outer edge of the bone thread path. If the surgeon determines that the second tap is undersized for the fifth metatarsal bone of the patient, the surgeon removes the second tap, inserts the third tap, and threads the distal tap thread portion of the third tap into the bone thread path in the intramedullary canal of the distal fragment. As with the second tap, the distal tap thread portion of the third tap is configured to preserve the bone thread path while also axially enlarging an outer edge of the bone thread path.

Once the surgeon determines the proper screw size using the tap, the surgeon can implant the proper size final screw implant. For example, if the second tap was the correct size, the surgeon inserts the second screw through the proximal bone fragment and threads the thread portion of the second screw into the bone thread path to thereby fix the proximal bone fragment to the distal bone fragment. Likewise, if the third tap was the correct size, the surgeon implants the third screw as the final screw implant.

The steps of inserting and threading the taps into the fifth metatarsal are preferably carried out through appropriately sized tissue protectors to thereby protect nearby tissues in the patient. Additionally, a guide pin is preferably used in the steps of inserting and tapping. Methods of inserting and using the guide pin are described below, along with details of various other aspects of preferred methods for successfully implanting the set of screws to fix Jones fractures.

As indicated above, the set of taps can be used to determine the size of a final screw implant during surgery rather than prior to surgery. Additionally, in a preferred embodiment the taps are configured for determining a proper length of a final screw implant. Each tap is provided with a plurality of length indicia relative to a distal tip of the tap. When the final tap is in a selected desired position corresponding to the final screw implant, the surgeon measures a final screw length by referencing the grooves in the tap against a length reference position on a tissue protector. Other methods of determining a final screw length include measuring the guide pin using a depth gauge, with the guide pin positioned such that the tip of the guide pin approximates a location of a tip of a final screw implant. Alternatively, a screw can be placed screw externally on a lateral side of the foot of the patient, and the surgeon verifies under external imaging that the selected screw is a proper screw length for the final screw.

The foregoing and other objects, features, aspects and advantages of the invention will become more apparent from the following detailed description of the invention when considered in conjunction with the accompanying drawings.

PREFERRED EMBODIMENTS OF THE INVENTION

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Figure 1:
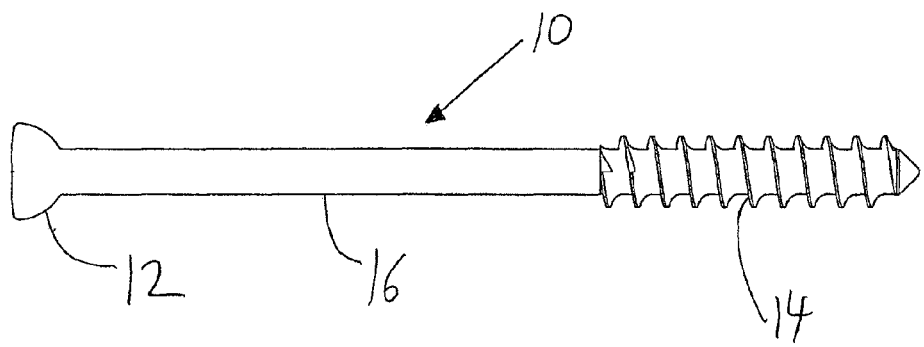
FIG. 1 is a side view of one preferred embodiment of a screw of the invention.
Figure 2:
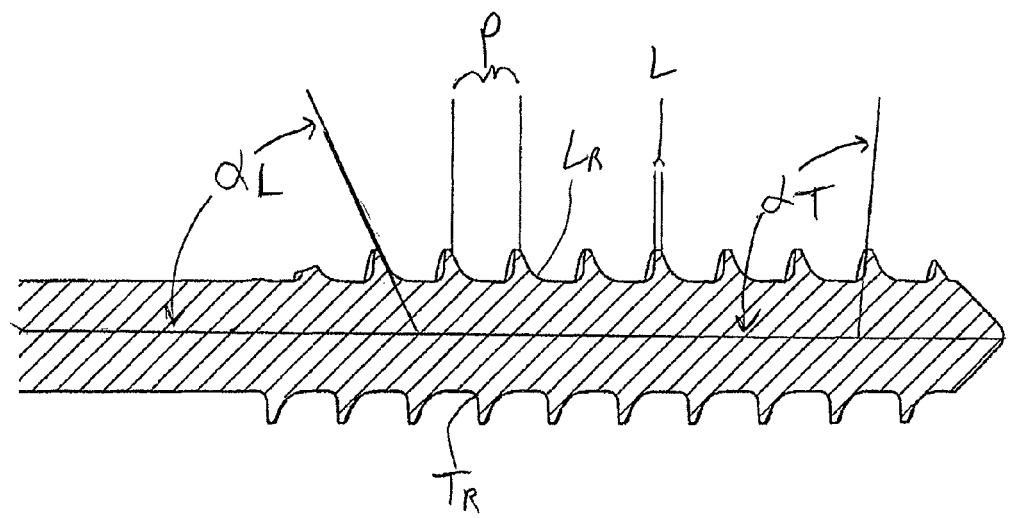
FIG. 2 is a side cross-section view of one preferred embodiment of a thread portion of a screw of the invention.
Figure 3:
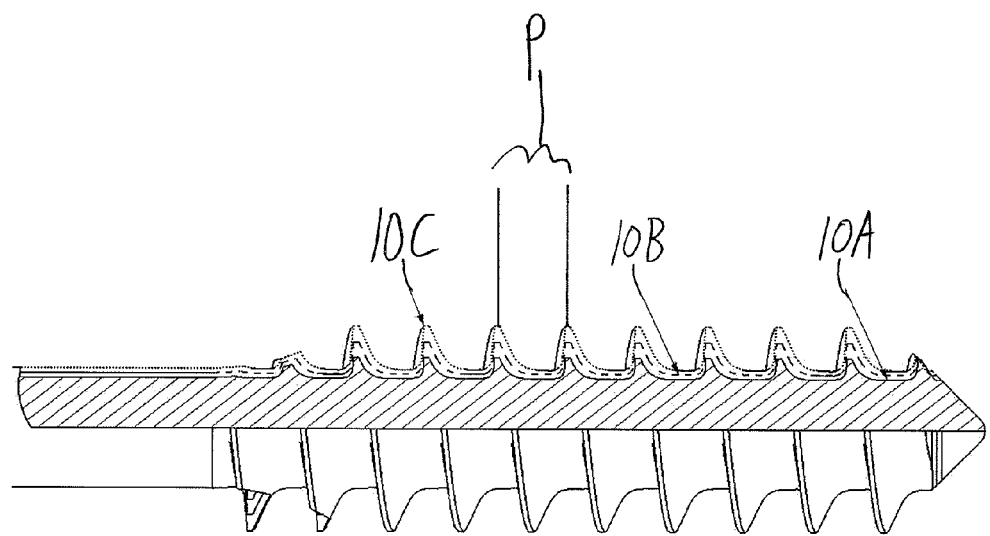
FIG. 3 is a side partial cross-section view of one preferred embodiment of the invention showing an overlay of thread portions of three sizes of screws according to a set of screws of the invention.

In general, the invention is a specialized screw system that allows surgeons to quickly and effectively treat challenging 5th Metatarsal fractures through MIS techniques with less potential for post-operative problems. The screw system of the invention includes a set of Jones screws having a particular set of dimensional characteristics. FIG. 1 shows a preferred embodiment of such a Jones screw 10. The screw 10 has a low profile head 12 on a trailing end, a thread portion 14 on a leading portion, and a smooth shank portion 16 between the head portion 12 and the thread portion 14. As shown in FIG. 3, an important characteristic of the screws 10 is that each screw 10A, 10B, and 10C in the set has the same thread pitch P (i.e. distance from crest-to-crest) as the other screws 10 in the set, but a different thread major diameter. Because the thread pitch P is the same on all of the screws 10, the surgeon can drill and tap upward to the required screw size in a bone preserving manner, as will be described in further detail below. The same thread pitch P reduces or eliminates cross-threading of the bone as the surgeon progresses from smaller to larger diameter screws, which improves bone purchase in comparison to screw sets that have different pitches.

The screws are provided in a range of sizes specific to the 5th metatarsal. The preferred sizes are 4.5 mm, 5.5 mm, and 6.5 mm, with the size referring to the major or outer thread diameter. In a preferred set of the screws, the 4.5 mm Jones screw 10 has a major or outer thread diameter of 4.5 mm, a shank diameter of 3.2 mm, and a thread minor or core diameter of 3.2 mm. The 5.5 mm Jones screw 10 preferably has a major/outer diameter of 5.5 mm, a shank diameter of 3.5 mm, and a thread minor/core diameter of 3.5 mm. The 6.5 mm Jones screw 10 preferably has a thread major/outer diameter of 6.5 mm, a shank diameter of 3.8 mm, and a thread minor/core diameter of 3.8 mm. The foregoing preferred diametrical relationships are derived from studies of 5th metatarsal anatomy, testing of screws in cadavers, and evaluation of deficiencies in existing bone screws. This set of screw configurations provides proper screw sizing, enables grasping of cortical bone, contributes (in combination with a constant pitch) to the option of sequentially tapping to a larger size when needed, and avoids piercing of the medial cortex. The shank and minor diameters are based on strength objectives, and are larger than the diameters of conventional cancellous bone screws.

The following table demonstrates how the diameter relationships of applicant's set of screws differ significantly from the diameter relationships of existing HA or HB thread form standards, as established by ISO 5835 and ASTM F543-02 specifications.

| all in mm | Applicant's preferred screw | | | ISO 5835 | | | ASTM F543-02 | | |
|---|---|---|---|---|---|---|---|---|---|
| Screw Type | Shank d | Core d | Thread Major d | Shank d | Core d | Thread Major d | Shank d | Core d | Thread Major d |
| 4.5 mm | 3.2 | 3.2 | 4.5 | n/a | 3 | 4.5 | n/a | 3 | 4.5 |
| 5.5 mm | 3.5 | 3.5 | 5.5 | n/a | n/a | n/a | n/a | n/a | n/a |
| 6.5 mm | 3.8 | 3.8 | 6.5 | 4.5 | 3 | 6.5 | 4.5 | 3 | 6.5 |

The screw sizing decision can be made in the operating room rather than prior to surgery. The surgeon can tap sequentially, checking size until cortical bone is engaged. Other dimensional characteristics provide the screw 10 with excellent strength, distal bite, and compression in order to ensure stability across the fracture site. These and other aspects of the invention provide significant advantages over prior art Jones screws.

Figure 5:
FIG. 5 is an external imaging view showing a preferred placement of the guide pin in the fifth metatarsal of the patient for use in a method of implanting screws for fixation of a Jones fracture according to the invention.

The concept of using a set of screws having equal pitches in bones is taught by U.S. Pat. No. 5,643,269 (Harle), which is incorporated herein by reference. Harle discloses the use of a set of equal pitch screws in vertebrae (see Harle, FIG. 5). Harle also discussed the use of equal pitch screws in tubular bone, such as when it is necessary to pass a screw through opposing cortexes of a tubular bone. However, Harle did not contemplate the use of same pitch screws as intramedullary implants in the manner of the present invention. Applicant is unaware of any teaching of the use of an equal pitch screw set in Jones fractures or in other intramedullary implant applications, nor of providing such a screw set with the dimensional relationships disclosed herein. Applicant's discovery of the benefits of using a same pitch screw set in Jones fractures, along with the other dimensional characteristics described herein, provides significant advantages over prior art Jones screws.

As can be seen from the above table, applicant's combination of shank diameter, core diameter (minor thread diameter), and thread major diameter (4.5, 5.5 and 6.5 mm) are not found in the ISO and ASTM standards. Providing a larger minor diameter than that specified in the ASTM and ISO standards results in better mechanical performance, such as in fatigue testing, and provides advantages over prior art designs, such as in resistance to screw breakage. Note that current ISO and ASM standards for bone screws do not describe an HB screw having a thread major diameter of 5.5 mm. As far as applicant is aware, a solid shank cancellous screw having a thread major diameter of 5.5 mm is not commercially available.

The thread 14 of the screws 10 is a sharp cancellous thread form. The sharp cancellous thread form would be characterized as an "HB" type bone screw under ASTM F543-02 and ISO 5835 standards. However, the thread form has a unique set of dimensional relationships and differs in several important respects from HA and HB screws described in ASTM F543-02 and ISO 5835. Although the threads of the 4.5 mm, 5.5 mm, and 6.5 mm screws 10 have different major and minor diameters from one another, the threads 14 all have the same pitch P, leading and trailing edge angles αL, αT, leading and trailing edge radii $L_r$, $T_r$, and land L. In a preferred embodiment, each screw 10 in the set has the following set of dimensions: pitch P 0.088 inches (2.2 mm); leading edge angle αL 65 degrees; trailing edge angle αT 95 degrees; leading edge radius $L_r$, 0.032 inches (0.8 mm); trailing edge radius $T_r$, 0.012 inches (0.3 mm); land L 0.007 inches (0.18 mm). The surfaces of the leading and trailing edges of the thread are preferably substantially flat except in the regions of the leading and trailing radii $L_r$, $T_r$. Through experimental work, the foregoing set of dimensional relationships has been determined to provide an optimal thread configuration for use in Jones fractures. When this set of dimensions is combined with screws having the thread major and minor diameters described above, the result is a screw set that is optimized for repair of Jones fractures.

Some variation can be made in the foregoing numbers without departing from the spirit and scope of the invention. Preferred ranges include: a major diameter of between about 4.4 to about 4.6 mm for the smallest sized screw; a major diameter of between about 5.4 to about 5.6 mm for the middle sized screw; a major diameter of between about 6.4 to about 6.6 mm for the largest screw; a pitch of between about 0.08 to 0.1 inches (about 2 to about 2.5 mm); a leading edge angle αL of between about 60 to about 70 degrees; and a trailing edge angle αT of between about 90 to about 100 degrees. The leading edge radius $L_r$, trailing edge radius $L_T$, and land L are dependent on the major diameter, pitch, and edge angles, and change in a corresponding manner.

If the concepts of this invention are applied to the intramedullary canals that are smaller than the 5th metatarsal, it is expected that it will be desirable to use a series of same pitch screws having smaller major diameters, such as 3.0 mm, 3.5 mm and 4.5 mm, along with minor diameters that exceed ISO and ASTM specifications. Likewise, there may be larger intramedullary canals in which 7.0 mm is a preferred major diameter.

In order to accommodate different metatarsal sizes and surgical conditions, the Jones screws 10 are preferably provided in a variety of lengths. For Jones screw applications, each size of screw 10 (4.5 mm, 5.5 mm, and 6.5 mm) is preferably available in lengths ranging from 30 mm to 80 mm, preferably in 5 mm increments, and most preferably in lengths from 40 mm to 70 mm. For other intramedullary applications in smaller bones, use of same pitch screws in lengths of between about 20 mm to about 40 mm may be preferable.

The length of the thread portion 14 preferably varies between about 0.5 to about 1.0 inches (about 12.7 mm to about 25.4 mm), and preferably varies depending on the overall screw length. For a 40 mm long screw, the thread length is preferably about 0.550 inches (about 14 mm); for a 45 mm screw, about 0.620 inches (about 15.7 mm); for a 50 mm screw, about 0.690 inches (about 15.5 mm); for a 55 mm screw, about 0.760 inches (about 19.3 mm); for a 60 mm screw, about 0.830 inches (about 21.1 mm); for a 65 mm screw, about 0.900 inches (about 22.9 mm); and for a 70 mm screw, about 0.970 inches (about 24.6 mm). In the foregoing ratios, the thread length is about 35 percent of the total length of the screw. As used herein, "thread portion length" means the linear length of the thread portion relative to a longitudinal axis of the screw, rather than the helical length of the thread.

To assist with removal of the screw 10 from the patient after bone in-growth has occurred, a trailing end of the thread is preferably provided with reverse cutting flutes, which are configured for use in cutting bone during removal of the screw.

A failing of prior art Jones screws is that the screw head protrudes above the bone, where it causes irritation and sometimes requires removal to relieve patient discomfort. To overcome this problem, the screw 10 of the invention is provided with a low-profile head 14. As shown in FIG. 1, the low-profile head 14 preferably has a generally hemi-spherical configuration, with a generally flat trailing end and a generally spherical leading edge. The radius of the spherical leading edge preferably substantially matches the radius of the low profile head 14, and originates along the lengthwise axis between about 0 to about 0.03 inches (about 0 to about 0.76 mm) from the trailing end of the head 14. The low-profile head 14 preferably has an outer diameter of between about 0.27 inches (7.0 mm) to about 0.35 inches (9.0 mm). The low-profile head 14 of the 4.5 mm screw 10 preferably has an outer diameter of 0.284 inches (7.2 mm) and a bottom head radius of 0.132 inches (3.4 mm). The low profile head 14 of the 5.5 mm screw preferably has an outer diameter of 0.292 inches (7.4 mm) and a leading edge radius of 0.146 inches (3.7 mm). The low profile head 14 of the 6.5 mm Jones screw 10C preferably has an outer diameter of 0.319 inches (8.1 mm) and a leading edge radius of 0.162 inches (4.1 mm).

The screws 10 are manufactured from solid-core surgical grade stainless steel for maximum strength, stiffness and fatigue life. A solid core stainless steel screw with high fatigue strength results in less screw breakage, potentially less screw removal, and possible early return to activity. Early results of fatigue testing indicate that the screws 10 of the invention are significantly more fatigue resistant than corresponding sizes of standard stainless steel malleolar screws or stainless steel cannulated screws. It is expected that applying the foregoing features to a solid titanium screw would provide similar advantages over cannulated titanium screws. Because titanium is less stiff than stainless steel, the use of solid titanium Jones screws 10 may be favored in high level athletes or other individuals who regularly subject the fifth metatarsals to high levels of stress. Additionally, although the use of the screws 10 has been described with reference to intramedullary procedures in the 5th metatarsal, it is anticipated that screws having the features described herein could be used in other bones and in other situations, such as for cortical and bi-cortical applications (e.g. Lisfranc), and that the features could be used with cortical screws having an HA configuration.

Instrument Set

The instruments and implants used in the procedure of the invention will typically be provided in the form of a surgical kit. In a preferred embodiment, the instrument set includes the following: cannulated drill (preferably 3.2 mm) and solid-core drill (preferably 3.2 mm); solid and cannulated taps (preferably 4.5 mm, 5.5 mm and 6.5 mm); tissue protector for use with a K-wire (preferably 2.0 mm); tissue protector for use with a drill and the 4.5 mm tap; tissue protector for use with the 5.5 mm tap; tissue protector for use with the 6.5 mm tap; a general purpose tissue protector; a 4.5 mm Jones screw; a 5.5 mm Jones screw; 6.5 mm Jones screw. The components of the kit are preferably arranged in a convenient format, such as in a surgical tray or case. However, the kit components do not have to be packaged or delivered together, provided that they are assembled or collected together in the operating room for use at the time of surgery.

Although the taps 20 have the form of a conventional bone screw tap, the taps differ in that they are configured to form a bone thread path in the 5th metatarsal that has the same thread pitch as the screws 10. The taps 20 have the same major and minor diameters as the corresponding sized screw 10. However, the taps 20 all have the same pitch P, leading and trailing edge angles αL, αT, leading and trailing edge radii $L_r$, $T_r$, and land L as the screws 10. Because the taps 20 have the same pitch and thread form characteristics as the screws 10, the taps can be used in series (i.e. 4.5 mm first, 5.5 mm second, 6.5 mm last) without damaging the bone thread path.

Surgical Technique

Surgery is performed under a regional block anesthesia. A tourniquet is usually used to provide a bloodless field, especially when an open technique is used. The patient is positioned supine with a bump under the ipsilateral hip so that the body is rotated toward the side of the operating room table that corresponds to the non-affected foot. Make sure that the ipsilateral knee can be flexed so that it may be placed plantigrade on the edge of the table or sterile operating room fluoroscopy unit or other external imaging device. Place a K-wire on the lateral aspect of the foot and use fluoroscopy or other external imaging to position the pin overlapping and parallel to the metatarsal shaft. This position should correspond to the target screw placement on both AP and lateral images. Trace two lines on the skin that correspond to the pin alignment in both views.

Figure 4:
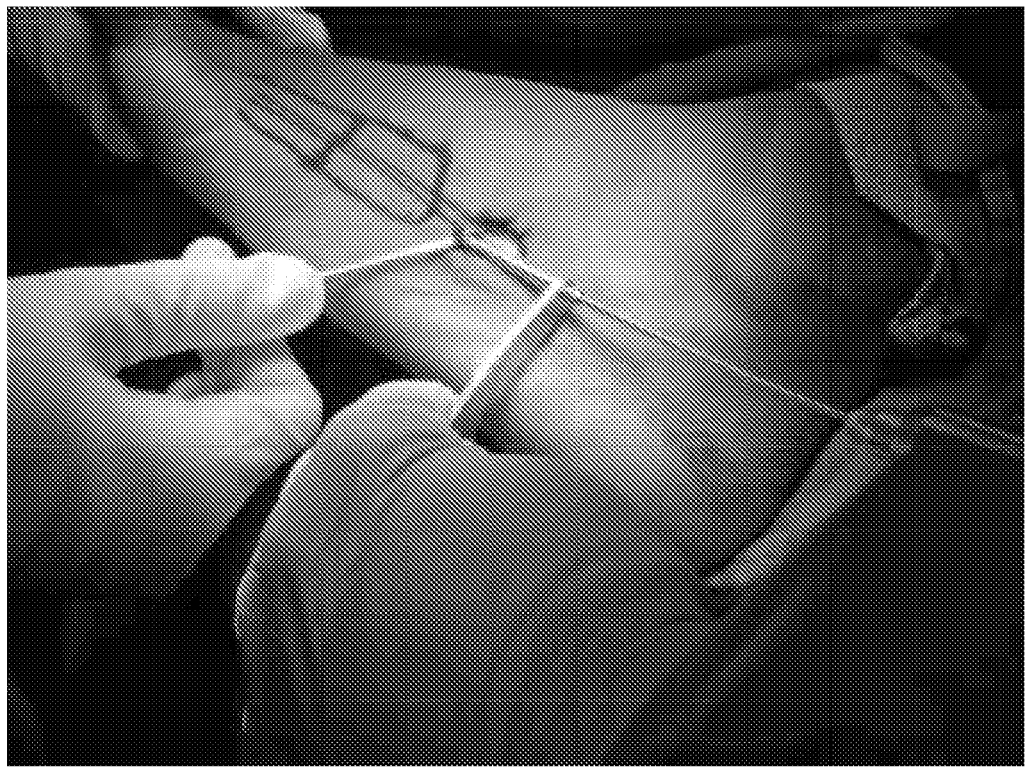
FIG. 4 is a perspective view showing placement of a guide pin for use in a method of implanting screws for fixation of a Jones fracture according to the invention.

Make a 1-2 cm extensile incision approximately 2 cm proximal to the base of the 5th metatarsal. Identify and protect the sural nerve and peroneus brevis tendon. Using the tissue protector, insert the guide pin high and inside on the base of the 5th metatarsal. (See FIG. 4). Creating the screw entry point high and inside on the proximal fragment allows proper intramedullary screw placement. The guide pin will be opposed to the lateral aspect of the cuboid. Use fluoroscopy to direct the tip of the pin into the center of the intramedullary canal, continuously checking AP, lateral and oblique views. Advance the pin to ½ the length of the shaft, or at a minimum just past the fracture line. To prevent deviating medially, the proximal end of the pin should lie against the lateral calcaneal skin while being advanced. (See FIG. 5).

Figure 6:
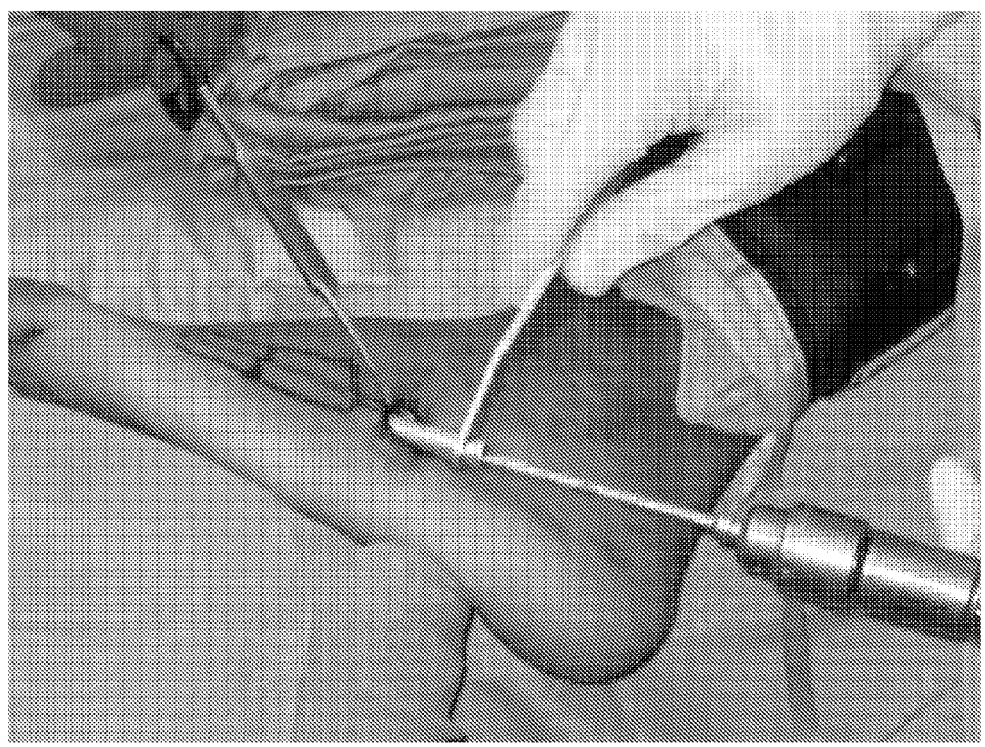
FIG. 6 is a side perspective view showing use of a tissue protector and a cannulated drill on the guide pin to prepare the fifth metatarsal for fixation of a Jones fracture according to the invention.

Using the tissue protector and continuous fluoroscopic guidance, advance the cannulated drill, avoiding penetration of the 5th metatarsal cortex. (See FIG. 6). Because the 5th metatarsal is not a straight bone, the guide pin may tend to curve; this will limit advancement of the drill. In this case, redirect the pin prior to further drilling. In an alternative drilling technique, use the cannulated drill to enter the proximal cortex only. Remove the guide pin and drill with the solid ⅛" drill, advancing continuously under fluoroscan until proper depth is obtained. Use of this technique decreases the risk of perforation or damage to the guide pin or cannulated drill.

Figure 7:
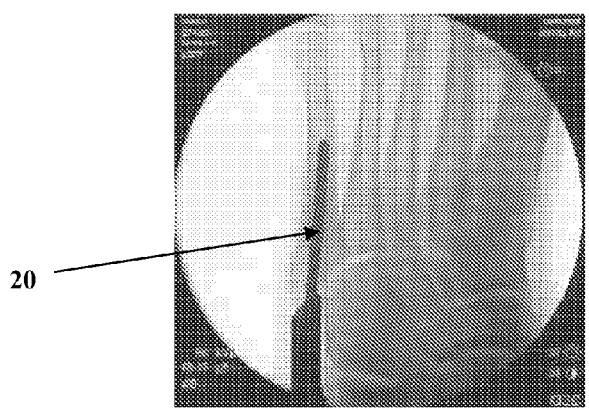
FIG. 7 is a external imaging view showing a step of using a tap for forming a thread path and selecting a final screw implant size in a method of the invention.

The tap should be advanced through the straight portion of the distal fragment in A/P and lateral views. Care should be taken not to advance into the curved portion, which could malreduce the fracture. Using the 4.5 mm cannulated tap and tissue protector, tap to the intended screw length. (See FIG. 7) The tap can be considered a trial, since the profile of the tap is the same as the screw. The tap should feel snug within the intramedullary canal. If the diameter is undersized, tap to the next size screw using the 5.5 mm cannulated tap and tissue protector. Check under fluoroscan. If the diameter is still undersized, continue sequentially tapping with the 6.5 mm cannulated tap and tissue protector.

When the correct tap is in the desired position, measure the screw length from the grooves in the tap against the tissue protector. Check with fluoroscopic imaging to be sure that the angled tip of the tissue protector is seated securely against the proximal 5th metatarsal bone. In an alternative measuring technique, the guide pin can be used to measure the screw length. If using the guide pin to measure screw length, the guide pin must be advanced until its tip approximates the location of the tip of the screw. Use the depth gauge to determine the screw length. In another alternative measuring technique, place a screw of the estimated length on the lateral side of the foot and check with fluoroscopic imaging that the proper length was chosen. This later technique is especially helpful when the fracture is quite distal because it helps confirm that all the threads are distal to the fracture line.

Figure 8:
FIG. 8 is an external imaging view showing a Jones fracture reduced by a screw according to the screw set and methods of the invention.

Select the correct screw diameter and length. Using the driver, insert the screw until it is fully engaged. Use fluoroscan to check final screw placement. (See FIG. 8).

Postoperatively, the patient is splinted and kept non-weight bearing for two weeks. At the end of two weeks, the patient is allowed to begin progressive weight bearing in a removable boot and with a custom molded orthosis. By the sixth week, the orthosis is maintained, and the patient is transitioned to regular shoes with a stiff sole to reduce motion. Athletes are usually allowed to jog on a track by the fifth to sixth week, and most are back to sports by the seventh to eighth week.

The term "external imaging" is used herein to refer to fluoroscopic imaging and analogous technologies that allow surgeons to view the fifth metatarsal or other internal structures of a patient during surgery.

Use of an injectable bone graft such as mini IGNITE® Power Mix (available from applicant, Wright Medical Technology, Inc.) should be considered when using the screws 10. IGNITE® Injectable Stimulus for Small Bone Fracture Callus Formation is designed to percutaneously graft a fracture site through an 11 gauge needle, preserving the periosteal blood supply. The mini IGNITE® kit includes diluent for reconstituting the IGNITE® powder. The operating medical professional has the option of reconstituting the powder using the included diluent or patient's own bone marrow aspirate (BMA). The combination of osteoinductive demineralized bone matrix, osteoconductive calcium sulfate and osteogenic progenitor cells from the patient allows a healing response at the fracture site.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. A method, comprising:
   inserting a first tap of a plurality of taps into and through an intramedullary canal of a proximal bone fragment of a fifth metatarsal bone, the first tap having a thread major diameter between about 4.4 mm to about 4.6 mm, each of the plurality of taps having a distal tap thread portion with identical thread profile characteristics to a corresponding one of a plurality of screws in which each screw has a low profile head on a trailing end, a thread portion on a leading portion, and a smooth shank portion between the head portion and the thread portion, the identical thread profile characteristics comprising a pitch, a leading edge angle, a trailing edge angle, a leading edge radius, a trailing edge radius, and a land;
   threading the distal tap thread portion of the first tap into an intramedullary canal of the distal bone fragment, to thereby form a bone thread path in the intramedullary canal of the fifth metatarsal bone;
   determining that the first tap is undersized for the fifth metatarsal bone;

removing the first tap from the fifth metatarsal bone;

inserting a second tap of the plurality of taps into and through the intramedullary canal of the proximal bone fragment, the second tap having a thread major diameter between about 5.4 mm to about 5.6 mm; and threading the distal tap thread portion of the second tap into the bone thread path in the intramedullary canal of the distal bone fragment such that the distal tap thread portion of said second tap preserves the bone thread path while also axially enlarging an outer edge of the bone thread path.

2. A method for fixing a Jones fracture in a fifth metatarsal bone of a foot of a patient, the Jones fracture including proximal and distal fragments of the fifth metatarsal bone, comprising, providing a set of screws in which each screw has a low profile head on a trailing end, a thread portion on a leading portion, and a smooth shank portion between the head portion and the thread portion, the set including:

a first screw of said set of screws having a thread major diameter of between about 4.4 mm to about 4.6 mm, a second screw of said set of screws having a thread major diameter of between about 5.4 mm to about 5.6 mm, a third screw of said set of screws having a thread major diameter of between about 6.4 mm to about 6.6 mm, and said thread portion of all said screws in said set of screws having a set of identical thread profile characteristics, said set of identical thread profile characteristics comprising a pitch, a leading edge angle, a trailing edge angle, a leading edge radius, a trailing edge radius, and a land;

providing a series of taps, each said tap having a distal tap thread portion having said identical thread profile characteristics as said thread portion of each said screw, a first tap in said series of taps having a thread major diameter matching that of said first screw, a second tap in said series of taps having a thread major diameter matching that of said second screw, and a third tap in said series of taps having a major diameter matching that of said third screw, inserting said first tap into and through an intramedullary canal of the proximal bone fragment;

threading said distal tap thread portion of said first tap into an intramedullary canal of the distal bone fragment, to thereby form a bone thread path in the intramedullary canal of the fifth metatarsal bone;

determining that said first tap is undersized for the fifth metatarsal bone of the patient;

removing said first tap from the fifth metatarsal bone;

inserting said second tap into and through the intramedullary canal of the proximal bone fragment; and threading said distal tap thread portion of said second tap into the bone thread path in the intramedullary canal of the distal bone fragment such that said distal tap thread portion of said second tap preserves the bone thread path while also axially enlarging an outer edge of the bone thread path.

3. The method of claim 2, further comprising determining that said second tap is undersized for the fifth metatarsal bone of the patient, removing said second tap from the fifth metatarsal bone, inserting said third tap into and through the intramedullary canal of the proximal bone fragment, and threading said distal tap thread portion of said third tap into the bone thread path in the intramedullary canal of the distal fragment such that said distal tap thread portion of said third tap preserves the bone thread path while also axially enlarging an outer edge of the bone thread path.

4. The method of claim 2, further comprising inserting the second screw through the proximal bone fragment and threading the thread portion of the second screw into the bone thread path to thereby fix the proximal bone fragment to the distal bone fragment.

5. The method of claim 3, further comprising inserting the third screw through the proximal bone fragment and threading the thread portion of the third screw into the bone thread path to thereby fix the proximal bone fragment to the distal bone fragment.

6. The method of claim 2, further comprising, in the steps of inserting and threading the taps into the fifth metatarsal, inserting and threading each said tap through a tissue protectors to thereby protect nearby tissues in the patient.

7. The method of claim 2, further comprising, prior to said step of inserting said first tap into and through the intramedullary canal of the proximal bone fragment, accessing the fifth metatarsal of the patient by making an extensile incision approximately 2 cm proximal to a base of the fifth metatarsal, inserting a guide pin high and inside on the base of the fifth metatarsal, such that the guide pin is opposed to the lateral aspect of the cuboid, to thereby guide proper screw placement in subsequent steps of the method, directing a tip of the guide pin into a center of the intramedullary canal while continuously checking AP, lateral and oblique views under external imaging, and advancing said tip of the guide pin to at least past a fracture line between the first and second bone fragments.

8. The method of claim 7, further comprising using said guide pin in said steps of inserting and tapping.

9. The method of claim 8, further comprising, prior to said step of inserting said first tap, advancing a cannulated drill into the fifth metatarsal on said guide pin under external imaging to thereby avoid penetration of a cortex of the fifth metatarsal.

10. The method of claim 8, further comprising removing said cannulated drill, removing said guide pin, and advancing a solid drill into the fifth metatarsal under external imaging until a selected proper depth is obtained.

11. The method of claim 7, further comprising laying said guide pin against a lateral calcaneal skin area of the patient while inserting said guide pin into the fifth metatarsal to thereby prevent the guide pin from deviating medially.

12. The method of claim 2, further comprising injecting a bone graft into the fifth metatarsal in conjunction with said set of screws to thereby assist in fixing the fracture of the fifth metatarsal bone.

13. The method of claim 2, further comprising advancing a tap through the straight portion of the distal fragment under external imaging, while not advancing said tap into a curved portion of the distal fragment in order to avoid malreduction of the Jones fracture.

14. The method of claim 2, further comprising determining which of said screws is a final screw size to be implanted in the patient by determining which of said taps is a final tap corresponding to said final screw size, wherein the step of determining a final screw size takes place during surgery rather than prior to surgery.

15. The method of claim 14, further comprising using said final tap to determine a length of a final screw to be implanted in the fifth metatarsal.

16. The method of claim 15, wherein each said tap is provided with a plurality of length indicia relative to a distal tip of said tap, and wherein said step of measuring further comprises, when said final tap is in a selected desired position, measuring a final screw length from the grooves in the tap against a length reference position on a tissue protector.

17. The method of claim 16, further comprising verifying under external imaging that a tip of said tissue protector is seated securely against the proximal fifth metatarsal bone, to thereby avoid an incorrect measurement.

18. The method of claim 7, further comprising determining a length of a final screw to be implanted in the fifth metatarsal by measuring said guide pin using a depth gauge, with the guide pin positioned such that said tip of said guide pin approximates a location of a tip of a final screw implant.

19. The method of claim 2, further comprising determining a length of a final screw to be implanted in the fifth metatarsal by selecting a screw from said set of screws, placing said selected screw externally on a lateral side of the foot of the patient, and verifying under external imaging that said selected screw is a proper screw length for said final screw.

20. The method of claim 19, further comprising confirming under external imaging that all of said thread portion of said selected screw placed externally on the lateral side of the foot of the patient is distal to a fracture line of the Jones fracture.

* * * * *